United States Patent [19]

McNamara et al.

[11] Patent Number: 5,620,446

[45] Date of Patent: Apr. 15, 1997

[54] SURGICAL APPARATUS FOR PERFORMING ENDOSCOPIC SURGERY AT LOCATIONS WHERE TISSUE INSERTS INTO BONE

[75] Inventors: Gregory McNamara, Lowell, Mass.; William E. Donahue, Mayfield Heights, Ohio

[73] Assignee: Endoscopic Heel Systems, Inc., Lowell, Mass.

[21] Appl. No.: 481,841

[22] Filed: Jun. 7, 1995

Related U.S. Application Data

[60] Continuation-in-part of Ser. No. 84,859, Jun. 29, 1993, Pat. No. 5,429,117, which is a division of Ser. No. 914,192, Jul. 14, 1992, Pat. No. 5,253,659.

[51] Int. Cl.$^6$ .................................................. A61B 17/00
[52] U.S. Cl. ........................... 606/79; 606/167; 606/170; 606/190; 604/104; 604/28; 128/898; 128/4
[58] Field of Search .................................. 604/104, 170, 604/28; 606/79, 167, 170, 190; 128/898, 3–4

[56] References Cited

U.S. PATENT DOCUMENTS

| | | |
|---|---|---|
| 4,497,320 | 2/1985 | Nicholson et al. . |
| 4,819,620 | 4/1989 | Okutsu . |
| 4,888,000 | 12/1989 | McQuilkin et al. . |
| 5,009,643 | 4/1991 | Reich et al. . |
| 5,029,573 | 7/1991 | Chow . |
| 5,253,659 | 10/1993 | McNamara et al. . |
| 5,269,290 | 12/1993 | Barrett et al. . |
| 5,273,024 | 12/1993 | Menon et al. . |
| 5,282,816 | 2/1994 | Miller et al. . |
| 5,312,360 | 5/1994 | Behl . |
| 5,429,117 | 7/1995 | McNamara et al. . |

OTHER PUBLICATIONS

Malay, D.S. Duggar, G.E. Heel Surgery, In Comprehensive Textbook of Foot Surgery, vol. 1, pp. 264–265 (1987).

Kenzora, J.E. The Painful Heel Syndrome: An Entrapment Neuropathy, Bull. Hosp. Joint Dis. Orthop. Surg. 47:178–189 (1987).

LaMelle, D.P. Chronic Plantar Fascial Inflamation and Fibrosis, Clin. Poc. Med. Surg., 7:385–388 (1990).

Bergmann, J.N. History and Mechanical Control of Heel Spur Pain, Clin. Pod. Med. Surg., 7:243–259 (1990).

Forman, W.M., Green M.A. The Role of Intrinsic Musculature in the Formation of Inferior Calcaneal Exostoses, Clin. Pod. Med. Surg., 7:217–233 (1990).

Snider, M.P., Clancey, W.G., McBeath, A.A. Plantar Fascia Release for Chronic Plantar Fascitis in Runners, Am. J. Sports Med., 11:215–219 (1983).

Lester, D.K., Buchanan, J.R. Surgical Treatment of Plantar Fascitis, Clin. Orthop. Rel. Res. 186:202–204 (1984).

Shmokler, R.L., Bravo, A.A., Lynch, F., Newman, L.M. A New Use of Instrumentation in Fluoroscopy Controlled Heel Spur Surgery, JAPMA, 78:194–197 (1988).

Polisner, R.I. Early Ambulation After Minimal Incision Surgery for Calcaneal Spurs, Clin. Pod. Med. Surg. 2:497–502 (1985).

Leach, R.J., Seavey, M.S., Salter, D. Results of Surgery in Athletes with Plantar Fascitis, Foot Ankle 7:156–161 (1986).

Ward, W.G., Clippinger, F.W. Proximal Medial Longitudinal Arch Incision for Plantar Fascia Release, Foot Ankle 8:152–155 (1987).

Hoffman, S.J., Thul, J.R. Fractures of the Calcaneus Secondary to Heel Spur Surgery, J.A.P.M.A. 75:267–271 (1985).

*Primary Examiner*—Randall L. Green
*Assistant Examiner*—Perry E. Van Over
*Attorney, Agent, or Firm*—Welsh & Katz, Ltd.

[57] ABSTRACT

An apparatus for performing endoscopic surgery at locations where tissue inserts into bone which includes cutting instruments having a novel knife blade with a blunted palpitation end to sever tissue without snagging while palpitating underlying tissue.

36 Claims, 10 Drawing Sheets

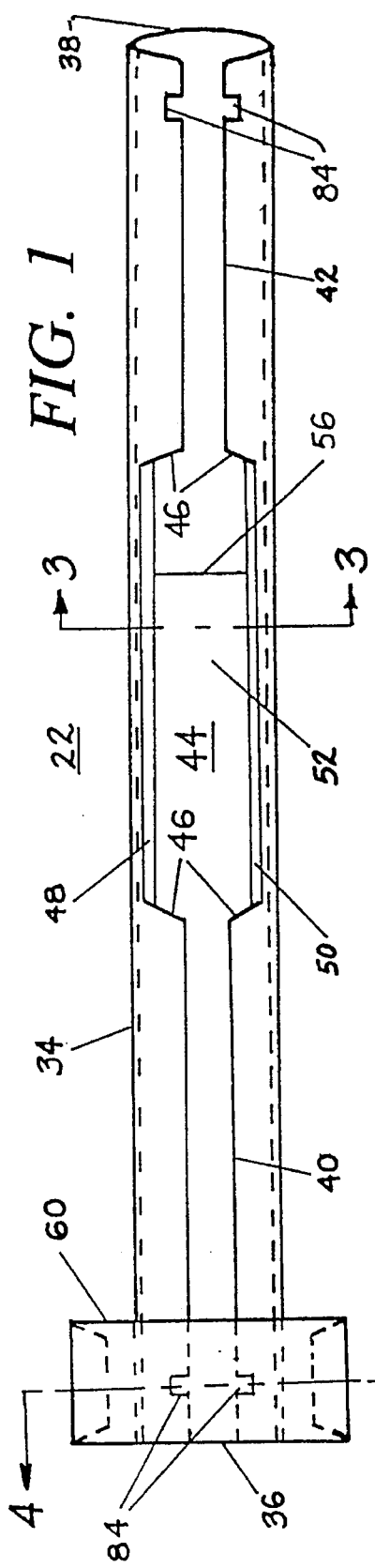
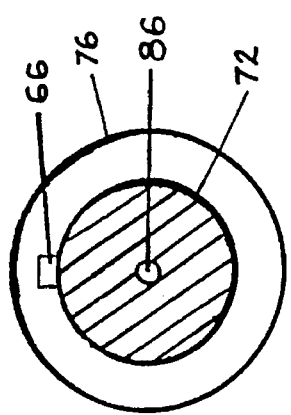
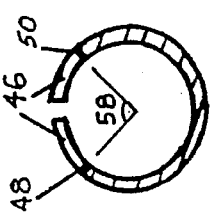
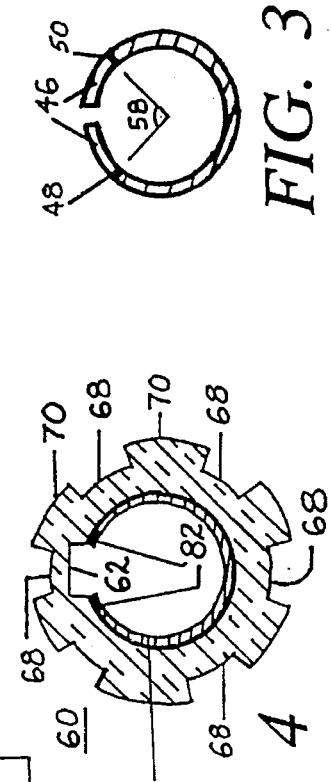
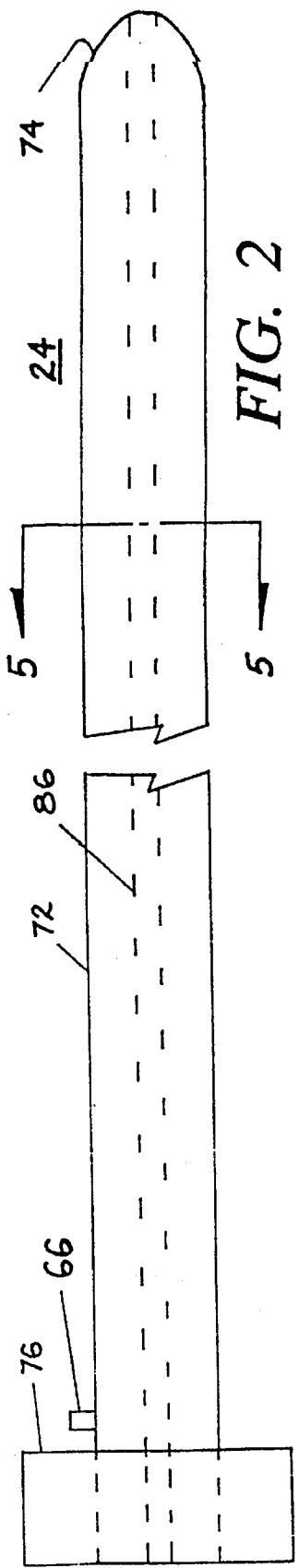

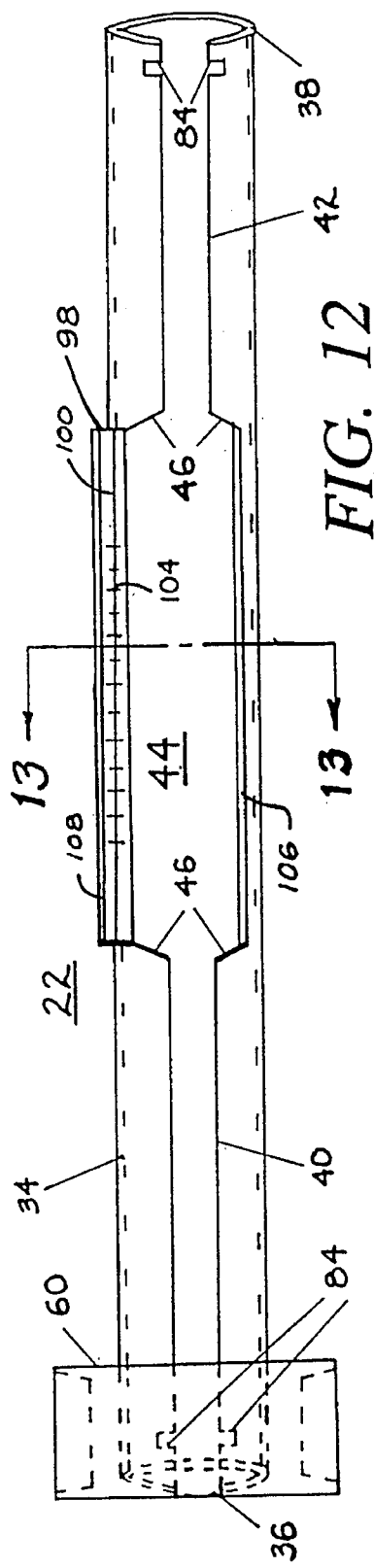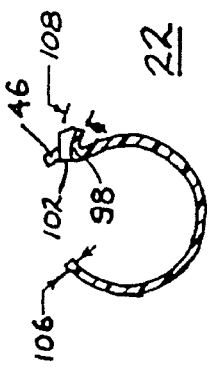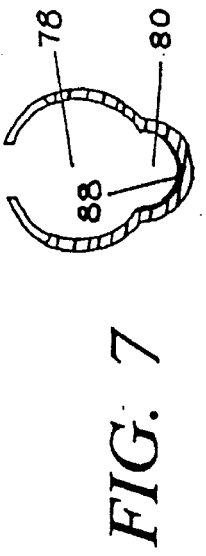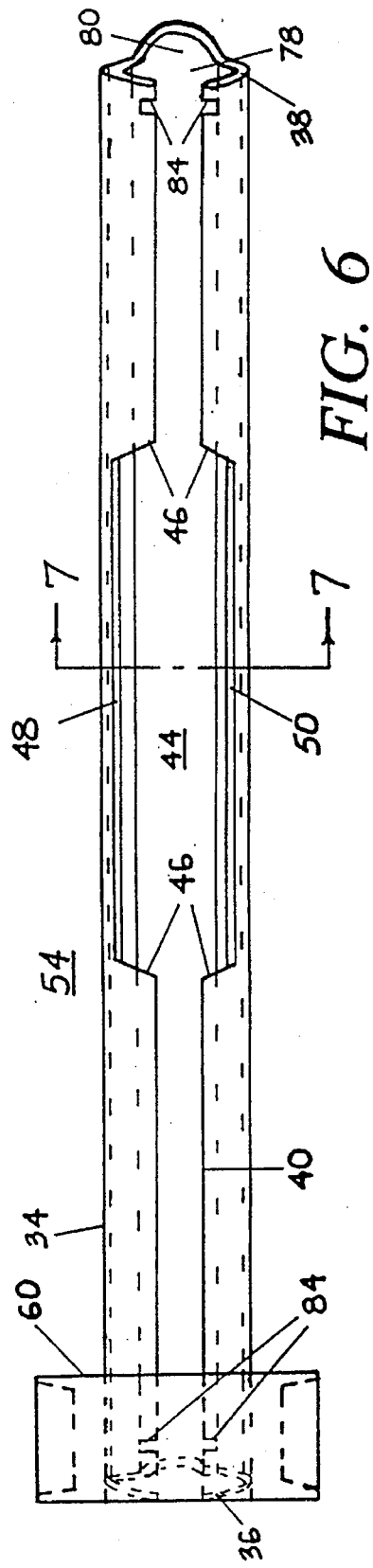

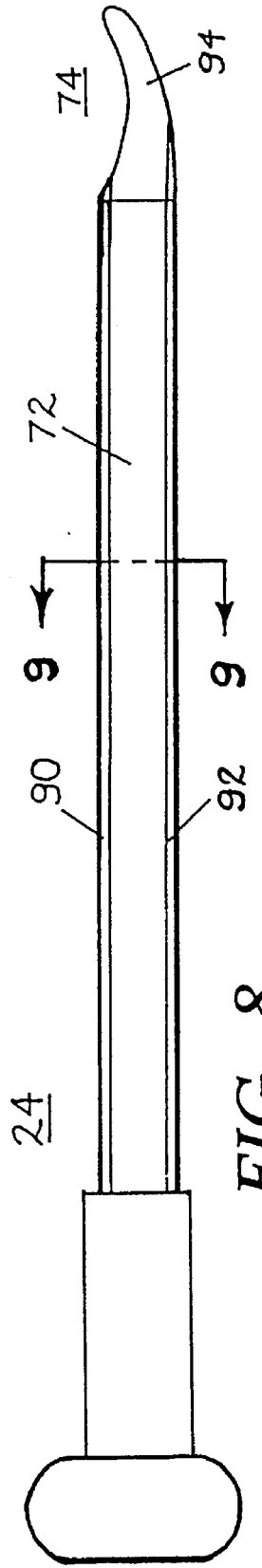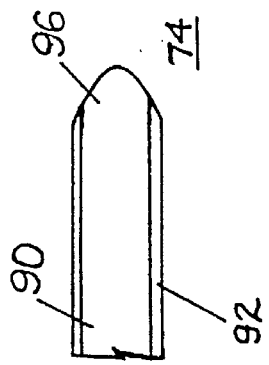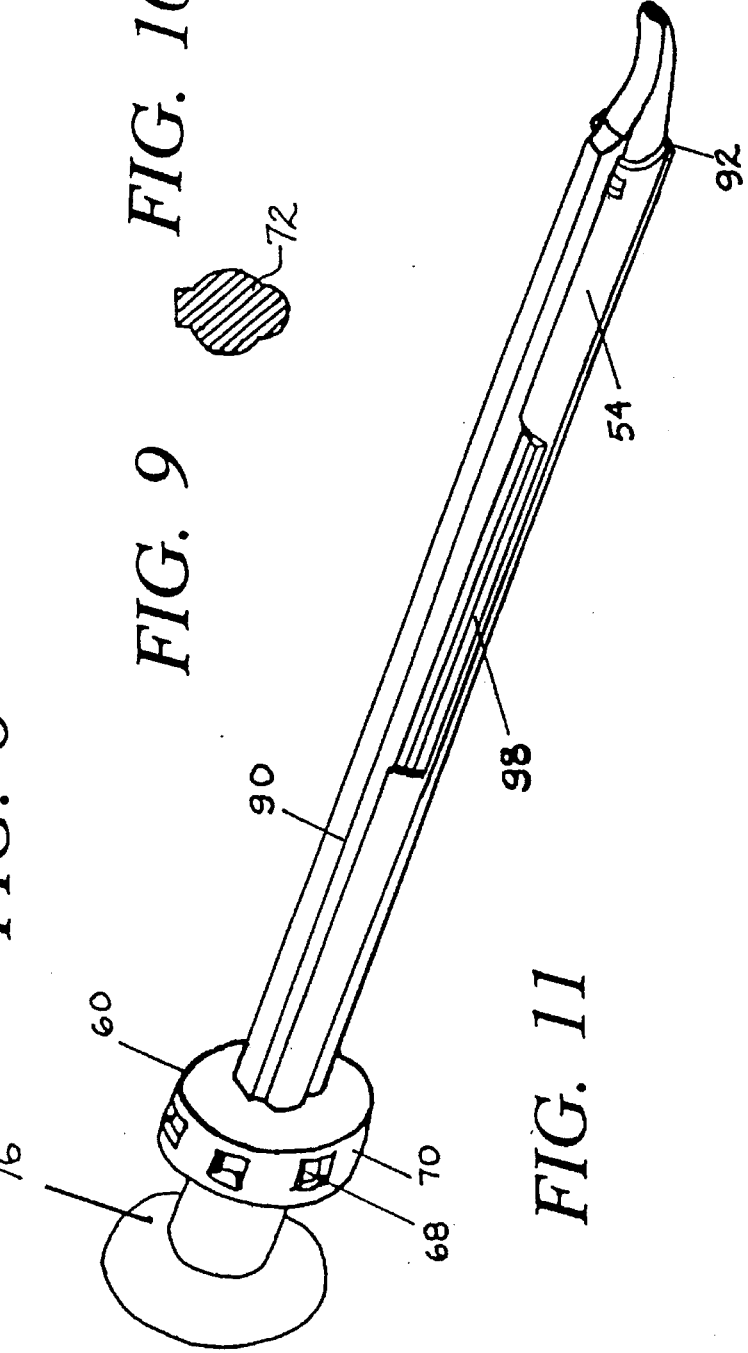
FIG. 8
FIG. 10
FIG. 9
FIG. 11

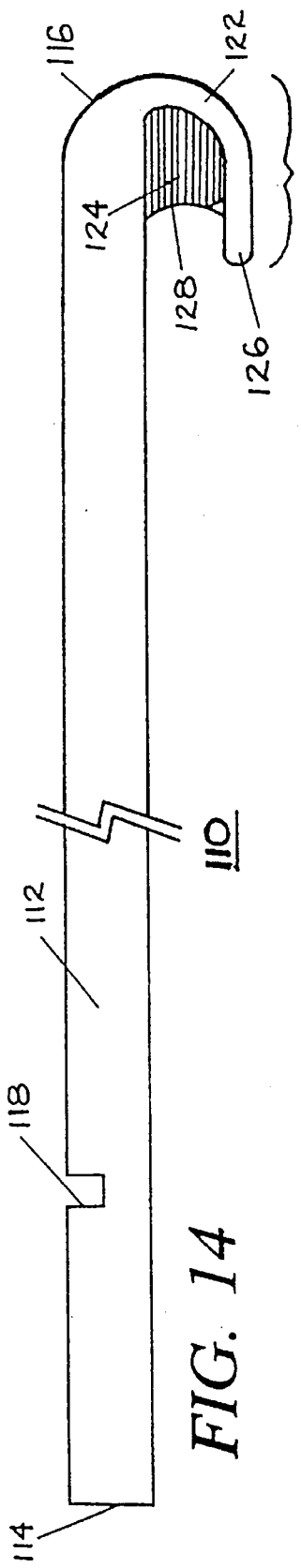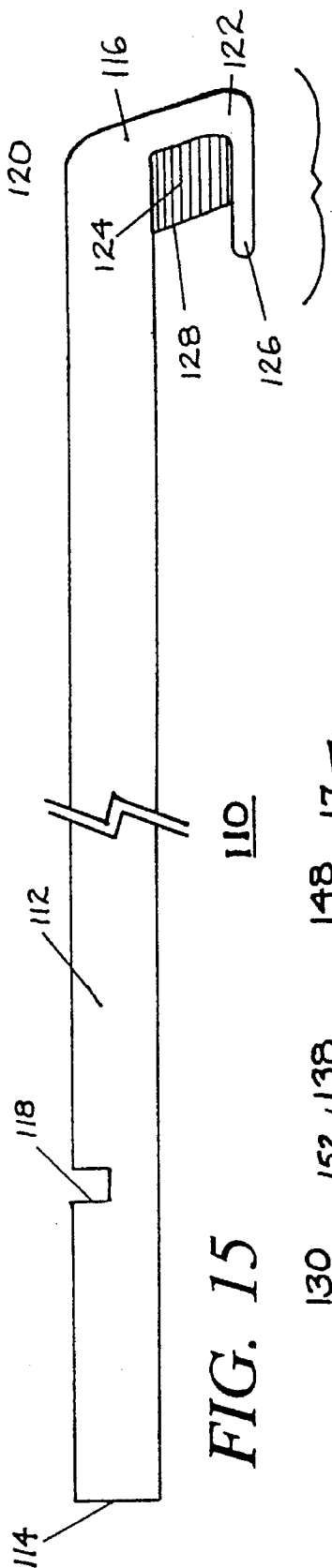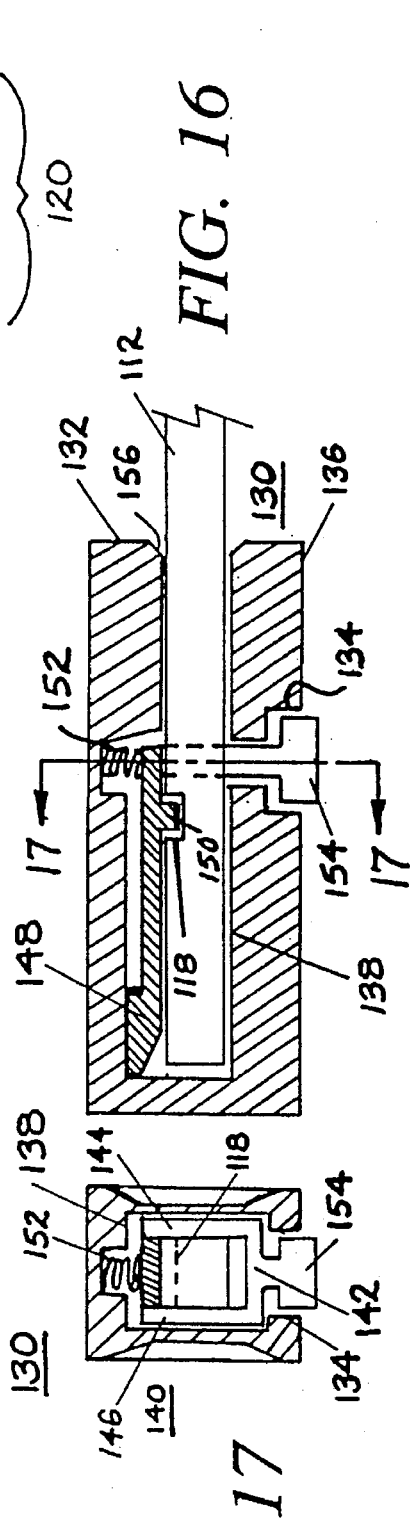

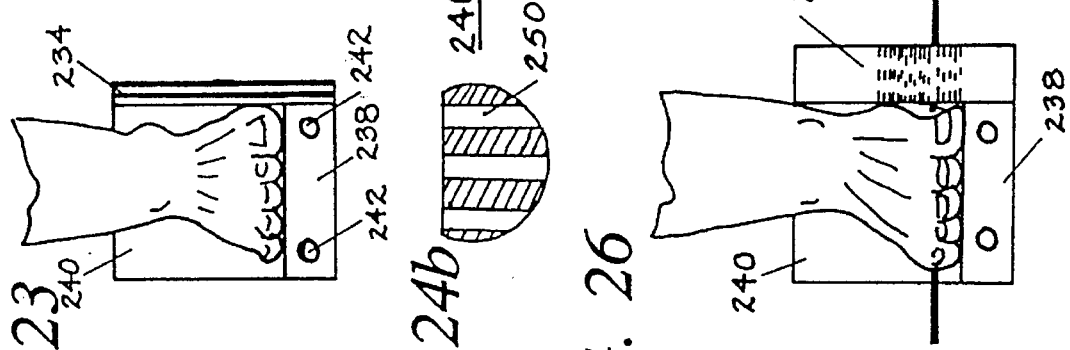
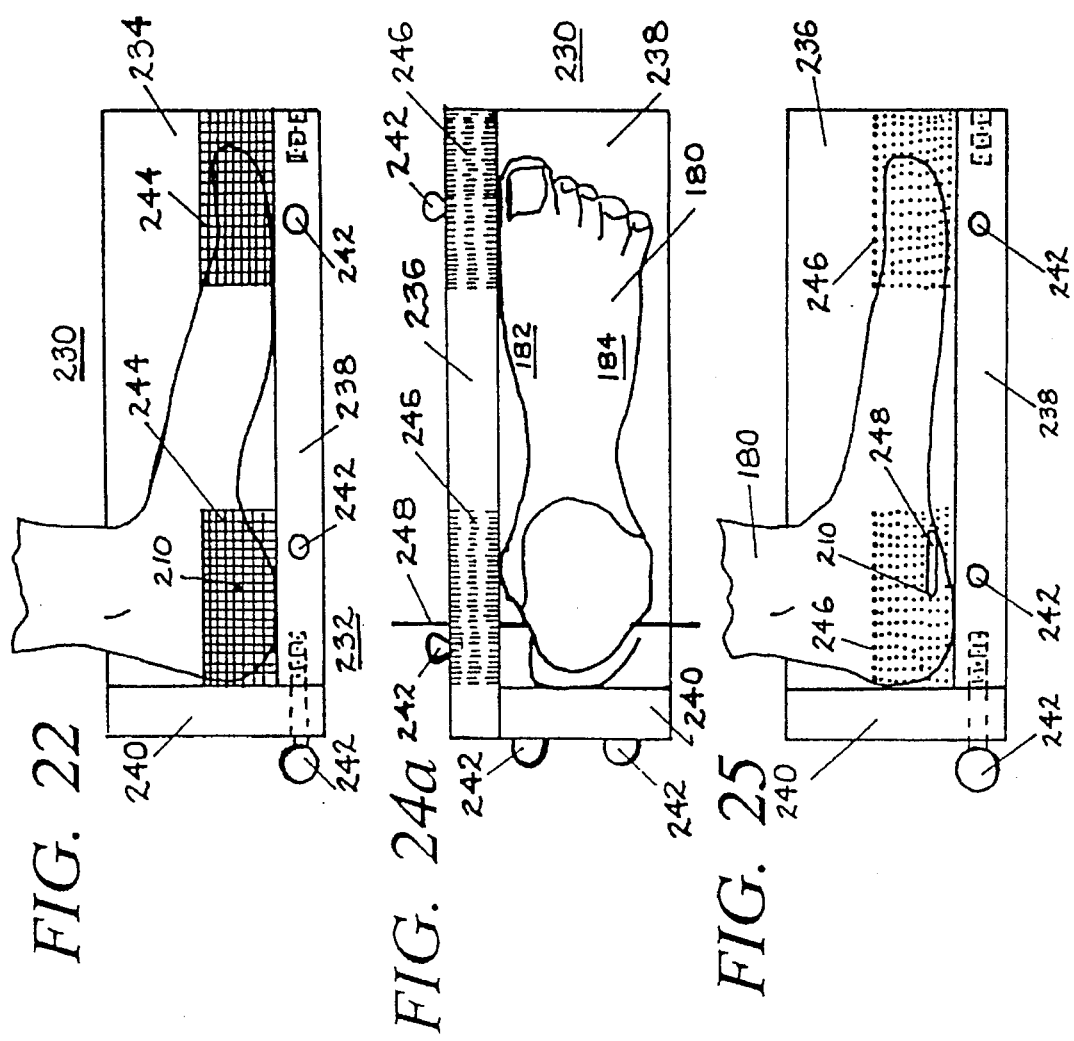

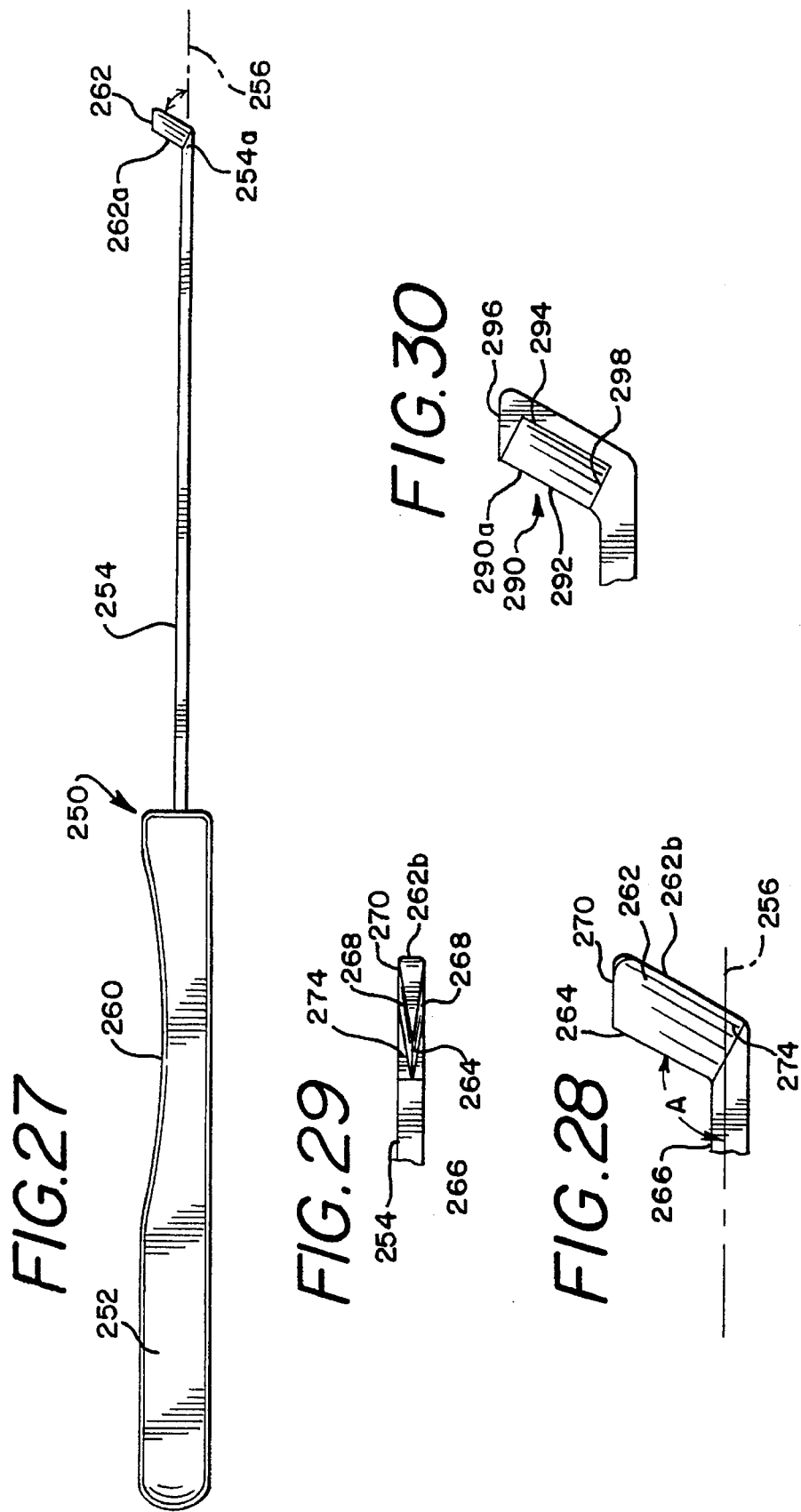

SURGICAL APPARATUS FOR PERFORMING ENDOSCOPIC SURGERY AT LOCATIONS WHERE TISSUE INSERTS INTO BONE

FIELD OF THE INVENTION

This is a continuation-in-part of application Ser. No. 08/084,859, now U.S. Pat. No. 5,429,117 filed Jun. 29, 1993 which is a division of application Ser. No. 07/914,192, now U.S. Pat. No. 5,253,659, filed Jul. 14, 1992. The present invention relates to endoscopic surgery at locations in the body where tissue inserts into bone and more particularly to a method and apparatus of performing endoscopic heel surgery.

BACKGROUND OF THE INVENTION

Various techniques and systems for performing endoscopic surgery in the body have been developed wherein a tube or sleeve is extended into the body and endoscopic and surgical instruments are introduced into the exposed end of the tube. These systems provide instrument access and visualization of tissue targeted by a specific operation. Advances have been made at locations in the body where a natural channel or simple pathway can be formed by a tube having a slot or opening for identifying and operating on the target tissue.

However, at other locations in the body these known methods and systems for endoscopic surgery have problems providing access and visualization at or near a line of insertion of tissue to bone. Problems occur because most bones have an arcuate surface with the corresponding line of insertion curving away from the opening of the tube resulting in the diminished reach of instruments and imaging of the endoscope. Other disadvantages of known systems include diminished visualization of deep cuts in thick tissues, the ability to identify and operate on adjacent tissues often requiring repositioning of the tube. Furthermore, a repositioned tube may not provide the needed access or visualization of the specific operation. Repositioning has other disadvantages including requiring additional surgical time and procedures, larger incisions to maneuver the tube, and increased likelihood of damage to tissue or the like.

Thus, the development of method and system for use in endoscopic surgery of these arcuate bone surfaces and lines of insertion without the disadvantages of known methods and systems would advance the state of the art. In addition, these known endoscopic techniques and systems have not solved problems of the particular environment of the bone and tissue in the foot. As the human foot is the foundation for most movement, foot pain and discomfort can cripple and seriously reduce such movement.

Typically, adverse foot mechanisms coupled with factors such as obesity or various types of traumatic motion can lead to a painful heel syndrome or plantar fasciitis with or without a spur forming on the os calcis. The pain is located at a site where the plantar fascia inserts into the medial and/or lateral tubercle of the os calcis. The insertion site follows an arcuate surface of the os calcis that may have a radial component extending distally from both tubercles with a predilection towards the medial aspect of the foot. Problems arise because the foot is formed from a complex web of compact tissue and bone under considerable tension with no available natural channel.

Known endoscopic techniques have advocated forming a channel using sharp dissection or using systems that visualize and blindly resect tissue from one end of a tube. Each of these has the disadvantage of increasing the risk of severing vascular and neural structures around the heel. Various non-endoscopic surgical techniques have been put forth to relieve the painful heel syndrome. Solutions have ranged from the use of conservative measures such as orthotics to surgical intervention with varying results depending upon the patient and other factors. Surgical intervention includes forming large incisions at or around the heel, surgical exploration or dissection to reach the plantar fascia, release of the plantar fascia from the os calcis, and excision of the degenerated fascial tissue and/or spur.

Known methods of surgical intervention have frequent sequela related to the interruption of the anatomy of the heel such as problems from the division of the medial calcaneal nerve causing foot numbness, protracted post operative pain and discomfort, skin incision problems or painful scars on the bottom and medial aspect of the foot, the inability to ambulate, as well as incomplete release of the plantar fascia due to inadequate visualization of the operative site.

Thus, a need exists for a simple heel surgery that reduces surgical trauma without lengthening the recovery time. Thus it is desirable to develop a method and system for endoscopic surgeries targeting the insertion of tissue to bone that reduces the trauma of surgical intervention. The system should be able to overcome problems of the prior art to operate with greater precision than known before to minimize scaring, damage to tissues, identify a plurality of tissue and bone structures, and release tissue and/or resect bone.

The method and system should be adaptable to foot surgery with increased surgical precision, reduced trauma and damage to the vascular and neural structures for the remedy of plantar fascitis such as in fasciotomies, fasciectomies, biopsies and resections of a spur on the os calcis. It is desirable to form a system that can perform multiple operations and procedures for the release of the plantar fascia and reduction of bone spurs that reduces recovery time and damage.

SUMMARY OF THE INVENTION

Accordingly, it is an object of the present invention to provide a method and apparatus for endoscopic surgery at the insertion of tissue to bone that overcomes the many disadvantages of the prior art.

It is an object of the present invention to provide a method and apparatus for endoscopic surgery tissue and bone of the heel that overcomes many of the disadvantages of known surgical interventions.

An object of the present invention to provide a system of a simple and easily operable construction being capable of use in the various surgical techniques for the remedy of plantar fasciitis.

It is another object of the present invention to provide a method and apparatus for endoscopic surgery at the insertion of tissue into bone. The apparatus features an improved sleeve member with a portal configured for visualization of the insertion of tissue to bone. In brief, the method for performing endoscopic surgery at the interface of tissue and bone uses a sleeve member formed from an elongated tube with open ends and a portal. The tube may have slot segments extending inwardly from the open ends and the portal has edge portions interconnected to the slot segments located at a midportion of the elongated tube. The portal forms an expanded surgical site with the advantage of simultaneous access and visualization of the interface of tissue and bone.

It is an object of the present invention to provide the portal with a flange to both push away and hold tissue during the resection of bone.

It is an object of the present invention to provide a sleeve member where the portal has a measurement system for gauging the reduction of a spur to a desired dimension. The measurement system is advantageous for use in measuring and improving the precision of the resection of tissue and/or bone.

It is another object of the present invention to provide an improved sleeve member with a portal having instrument and register portions configured for use in operations involving excision of a section of the plantar fascia.

It is an object of the present invention to provide improved cutting instruments for division of the plantar fascia and other procedures with minimal trauma to the underlying tissues. In brief, the instrument has an elongated shaft with proximal and distal ends, a handle attached to the proximal end, and, optionally, a locking device for attaching the handle to the shaft. The distal end may have a rounded forward portion extending generally transverse from the shaft, or a forward portion extending at an angle to the shaft, a cutting portion and optionally, an extension at the lower end of the cutting portion for guiding between layers of tissue and palpitating tissue.

It is yet another object of the present invention to provide an instrument for excision of a section of the plantar fascia and other procedures with minimal trauma to the underlying tissues. In brief, the excision instrument has an elongated shaft with proximal and distal ends, a handle attached to the proximal end and optionally a locking device for attaching the handle to the shaft. The distal end has an operative portion provided with a cutting section and a gathering section. The cutting section has dual knives extending transverse from the shaft forming a slot releasing a section of tissue. The knives are spaced apart and offset at an angle relative to the longitudinal axis of the shaft. An extension at the lower end of the knives palpitates and guides between layers of tissue. The gathering section has a tooth means positioned within the slot for gathering and removing a released section of tissue.

It is an object of the present invention to provide a system and method of determination of entry and exit incision points in the heel for reducing damage to vascular and neural structures. It is an object of the present invention to provide a marking system for use with a lateral x-ray for precisely determining an entry incision.

It is yet another object of the present invention to provide an insertion system for guiding a pin through the foot.

In brief, a procedure is provided for performing endoscopic surgery in a patient to relieve a painful heel syndrome in a foot generally having a heel with skin, plantar fascia, vascular and neural structures, os calcis bone and muscles including the flexor digitorum brevis, abductus digiti minimi, abductus hallucis.

The procedure desirably includes the steps of forming an entry incision on one side of the foot; forming a channel in the foot extending interiorly of said entry incision between the os calceus, plantar fascia and the aponeurotic fibers of the muscles by bluntly separating the muscle belly or plantar fascia from surrounding soft tissue, while avoiding injury to the vascular and neural structures in the heel, by inserting and advancing through the entry incision a detachable obturator and sleeve member assembly, the obturator having a blunt distal end and the sleeve member having portals at either end portion thereof through which portions of the obturator and at least one instrument may pass and having at least one window area through which a portion of the at least one instrument may be exposed to the interior structure of the heel; forming an exit incision for a portion of the obturator and sleeve member assembly at the side of the foot opposite the entry incision; extending the channel through the exit excision by passing the blunt distal end of the obturator and the end portion of the sleeve member adjacent thereto through the exit incision; positioning the sleeve member in the channel with the window of the sleeve facing the interior surface of the foot in a selected direction, desirably by rotating the sleeve member in the channel by rotating the obturator while positioned in the sleeve member; withdrawing the obturator from the sleeve member if still present therein; inserting an instrument used for excising a portion of the foot structure through one of the portals of the sleeve member; positioning the instrument used for excising a portion of the foot structure with the excising portion thereof adjacent the portion of the foot structure to be excised through the window of the sleeve member, and manipulating the handle of the instrument to extend the excising portion thereof through the window and excising the portion of the foot structure to be excised.

The instrument for excising a portion of the foot structure or tissue, desirably comprises an elongated shaft having proximal and distal ends, a handle secured to the proximal end for use in manipulating the instrument, and the distal end having a generally blunt forward portion extending at an angle from the shaft and including an excising portion generally facing the proximal end of the shaft.

In another embodiment of the procedure, a location and mark for an entry incision is determined on a medial side of the foot for avoiding the vascular and neural structures. Once the entry incision is made, a channel is formed between the os calcis, the plantar fascia, the aponulotic fibers of the muscles by bluntly separating the plantar fascia from surrounding soft tissue both superiorly and inferiorly. The channel is formed to avoid the vascular and neural structures in the heel using a detachable obturator and sleeve member assembly. The assembly is inserted and driven from a medial side to a lateral side of the foot until the assembly tents the skin on the lateral side where an exit incision is made. The sleeve member and obturator are passed through to the lateral side of said foot to position and locate a portal of the sleeve member at a predetermined operative site. The predetermined operative site provides simultaneous visualization of the plantar fascia, the os calcis and the line of insertion of the plantar fascia into the os calcis. The obturator is retracted from the sleeve member forming a medial and lateral opening at each end of the sleeve member and leaving the sleeve member located at the predetermined operative site. An endoscope is inserted into the medial opening and an instrument into the lateral opening. One or more surgical operations are performed at the operative site. The operative site is cleaned, the obturator is reinserted and the obturator and sleeve member retracted. The entry and exit incisions are sutured closed after successful performance of the desired surgical operations.

BRIEF DESCRIPTION OF THE DRAWINGS

These and other objects and advantages of the present invention will become readily apparent upon consideration of the following detailed description and attached drawing, wherein:

FIG. 1 is an elevational view illustrating the sleeve member for use in the method and system for endoscopic heel surgery of the present invention;

FIG. 2 is a side view of the obturator assembly of the present invention;

FIG. 3, taken along lines 3—3 of FIG. 1, is a cross-sectional view of the sleeve member of the present invention;

FIG. 4, taken along lines 4—4 of FIG. 1, is a cross-sectional view illustrating the stop member;

FIG. 5, taken along lines 5—5 of FIG. 2, is a cross-sectional view of the obturator and central bore;

FIG. 6 is an elevational view illustrating an additional embodiment the sleeve member of the present invention;

FIG. 7, is a cross-sectional view, taken along lines 7—7 of FIG. 6, illustrating the biopsy and endoscope portions of the present invention;

FIG. 8, is a side view illustrating an additional embodiment of the obturator of the present invention;

FIG. 9, is a cross-sectional view, taken along lines 9—9 of FIG. 8, illustrating the additional embodiment of the obturator of the present invention;

FIG. 10 is a side view illustrating a blunt tip of the obturator of FIG. 8;

FIG. 11 is a perspective view illustrating a obturator and sleeve member of an additional embodiment of the present invention;

FIG. 12 is an elevational view illustrating a sleeve member for yet another embodiment of the present invention;

FIG. 13, taken along lines 13—13 of FIG. 12, illustrates a flange for use in reduction of calcaneal spurs;

FIG. 14 is a side view illustrating an instrument for dividing the plantar fascia according to the present invention;

FIG. 15 is a side view illustrating another instrument for dividing the plantar fascia according to the present invention;

FIG. 16 is a schematic side view illustrating a handle configured to receive an instrument according the present invention;

FIG. 17 is a schematic cross-sectional view, taken along lines 17—17 of FIG. 16;

FIG. 22 is a side view of the marking system according to the present invention;

FIG. 23 is an end view of the marking system in accordance with the present invention;

FIG. 24a is an elevational view and FIG. 24b is a schematic cross-sectional view of the insertion system of the present invention;

FIG. 25 is a side view of the insertion system of the present invention;

FIG. 26 is an end view of the insertion system of the present invention;

FIG. 27 is a side elevational view illustrating an alternate embodiment of the surgical apparatus used in conjunction with the method of the present;

FIG. 28 is an enlarged side view of a cutting end forming the part of the surgical apparatus of FIG. 27;

FIG. 29 is a top view of the cutting end of FIG. 28; and

FIG. 30 is a alternate embodiment of the cutting end of the surgical apparatus of FIG. 27.

DETAILED DESCRIPTION OF THE PREFERRED EMBODIMENT

Figure 18:
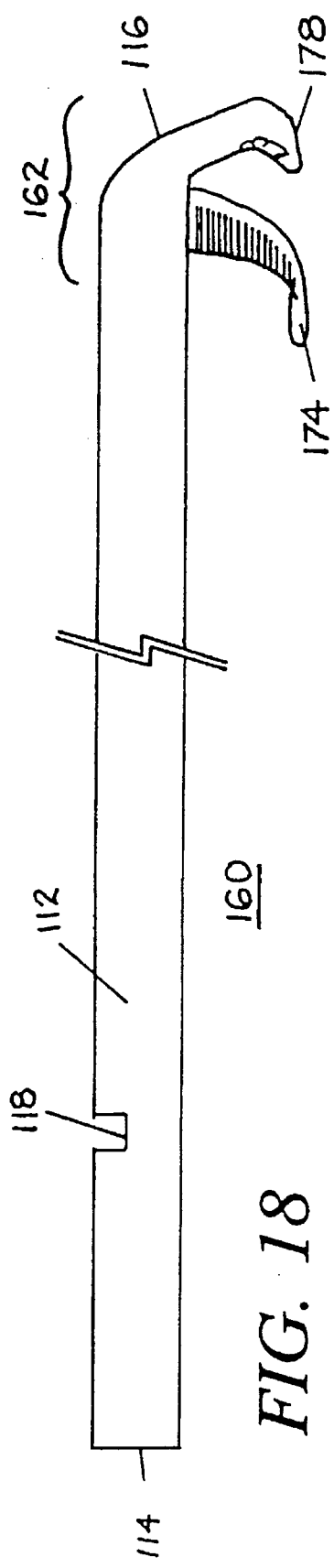
FIG. 18 is a side view illustrating another instrument for excision of the plantar fascia according to the present invention.

FIGS. 1–26, illustrate the preferred method and system of the present invention for the endoscopic release of the insertion of tissue into bone throughout the body. The present invention is described in the environment for treatment of the painful heel syndrome which can include neuritis, myositis, fascitis and adventitial bursitis with or without a calcaneal spur. The endoscopic release of the plantar fascia at its insertion into the os calcis and/or resection of spurs has been successful for relieving pain in the heel.

The endoscopic system 20 of the present invention includes generally a cannula or sleeve member 22, trocar or obturator 24, fasciotomy instrument 110, excision instrument 160 and a marking and insertion assembly 230. The sleeve member 22 provides an expanded portal 44 through which multiple surgical procedures such as a fasciotomy, fasciectomy, biopsy and heel spur resection can be performed at arcuate lines of insertion where tissue attaches to bone. Throughout the following detailed description, whenever possible the same reference numerals refer to like elements.

As illustrated in FIGS. 1, 3 and 4, the sleeve member 22 of the present invention includes an elongated tube 34 with open ends 36 and 38, and slot segments 40 and 42 extending inwardly from the open ends 36 and 38, respectively. A portal 44 is located at a mid portion of the sleeve member 22. The portal 44 is connected to slot segments 40 and 42 by tapper portions 46 to thus extend along the length of the elongated tube 34. The portal 44 further includes side edge portions 48 and 50 to form an access 52 to view the heel structures such as the os calcis, neurovascular structures and plantar fascia.

The access 52 allows an endoscope placed in, for example, open end 36 to form an image of these heel structures. The access 52 also allows an instrument placed in the other open end 38 for surgical utilization on these heel structures. The portal 44 can have width 56 determined by angle 58 so as to form an expanded view of the insertion of the plantar fascia into the os calcis and other heel structures. The sleeve member 22 should be made to extend from either side of the foot, for example, having a length dimension of 10 cm. The sleeve member 22 can be formed from suitable material such as non-reflective plastic to improve endoscopic imaging and to allow for the use of surgical lasers.

As shown in FIGS. 1, 2, 4 and 5, a collar or stop member 60 can be attached to end 36 of the sleeve member 22 to provide a grip when manipulating and as required for instruments or the like. The sleeve member 22 and stop member 60 are configured to receive slidably obturator 24. The stop member 60 includes a guide 62 located on an inner surface 64 of the stop member 60. The guide 62 engages a stem 66 on the obturator 24. The guide 62 and stem 66 are assembled to interlock for insertion into the heel and to indicate the alignment of the sleeve member 22. Recess points 68 on the exterior surface 70 of the stop member 60 can be used advantageously for single handed gripping or for gripping with a ratchet (not shown) to rotate the portal 44 of sleeve member 22 into position adjacent the operative site. The stop member 60 with tab portions 82 can interlock with nibble portions 84 adjacent either open end 36 or 38 of the sleeve member 22.

The obturator 24 includes a generally smooth shaft 72 with blunt tapered distal end 74 and handle 76 attached at the proximal end. The sleeve member 22 slidably receives the shaft 72 along the length thereof with the blunt distal end 74 protruding from end 38.

In operation, the obturator 24 and sleeve member 22 are inserted through the foot with the portal 44 positioned adjacent the insertion of the plantar fascia into the os calcis. Alternatively, the obturator 24 can have a central bore 86 along the length of the shaft 72 for use in engaging a guide wire 248 of the marking and insertion assembly 230 as described herein and shown in FIGS. 24, 25 and 26.

FIGS. 6, 7, 8 and 9 illustrate an additional embodiment of the present invention. The sleeve member 54 is particularly useful in when performing a fasciectomy or excision of sections of the plantar fascia and in biopsy of tissue. As best shown in FIG. 7, the sleeve member 54 has a non-uniform cross-sectional aperture with an instrument portion 78 and register portion 80. The larger dimension of the instrument portion 78 increases the working area to accommodate excision or biopsy instruments such as a rotary abrader, jaw-like forceps used in sampling tissue or other instruments. The register portion 80 can allow the surgeon to hold the endoscope against the arcuate surface 88 as a means for steadying during resection of tissue or bone spurs using a rasping instrument (not shown). The register portion 80 also provides increased space and maneuverability for instruments when operating on tissue or bone.

As shown in FIG. 8, the shaft 72 of obturator 24 can be slidably received in sleeve member 54 having upper protrusion 90 and lower protrusion 92 that engage the instrument and register portions 78 and 80, respectively. As shown in FIGS. 8 and 10, the obturator 24 can be advantageously configured with either a bill shaped dissector tip 94 or a blunt tip 96 at the distal end 74 for separating tissue.

FIGS. 11–13 illustrate another embodiment of the present invention particularly useful for endoscopic reduction of bone. The sleeve member 22 or 54 can include a flange 98 for engaging tissue along the line of insertion and exposing bone. The flange 98 can formed at the side edge portions 48 and 50 of the portal 44. As illustrated in FIG. 6, the flange 98 can be formed at the side edge portions 48 and 50 of sleeve member 54 with the flange 98 adjacent instrument portion 78 and spaced apart from register portion 80. A measurement portion 100 can also be used in conjunction with the flange 98 to gauge precisely the reduction or resection of bone. The measurement portion 100 can be formed adjacent side edge portions 48 and 50 that includes a gradient 102 and scale 104. The gradient 102 varies the dimension of the wall 106 forming edge portions 48 and 50 or the wall 108 of the flange 98. The scale 104 can be calibrated with the gradient 102 to provide a reference when reducing bone. The measurement portion 100 can be used advantageously in bone or spur removal to a greater precision than previously known in the art, thereby decreasing trauma and speeding recovery.

Referring now to FIGS. 14 through 17, the interchangeable cutting instruments provided with a detachable handle are described. In FIGS. 14 and 15, a fasciotomy instrument 110 for dividing the plantar fascia includes an elongated shaft 112 having opposing proximal and distal ends 114 and 116, respectively. The proximal end 114 can have a notch 118 configured for use with the locking and release feature of the handle 130.

Alternatively, instrument 110 may have a handle such as handle 252 in FIG. 27 secured to elongated shaft 112, in the same manner that handle 252 is secured to an elongated shaft 254 (FIG. 27) as hereinafter described in connection with the embodiment shown in FIG. 27.

The distal end 116 has an active portion 120 configured to improve the surgical operation of releasing the plantar fascia. The active portion 120 includes a hook portion 122 extending transversely from the shaft 112, a knife portion 124 along the interior of the hook portion 122 and a palpitation extension 126. The knife portion 124 can be formed in a concave shape 128 adaptive to center and cut the plantar fascia. The knife portion 124 also can be formed straight and angled relative to the elongated shaft 112 to provide for retrograde division from medial to lateral of the plantar fascia, as shown in FIG. 15. The palpitation extension 126 extends proximally beyond the knife portion 124 and is adapted to hook under and extravasate from the plantar fascia to palpitate the underlying fat pad during division of the plantar fascia.

As shown in FIGS. 16 and 17, the instrument handle 130 includes a shell 132, a recess 134 along surface 136 of the shell 132, and a chamber 138. The handle 130 features an activation system 140 for interchanging instruments with the handle 130 such as when used in the release of the plantar fascia. The activation system 140 includes a release member 142 having posts 144 and 146, rocker bar 148 with knob 150 and a spring 152. The release member 142 extends from the chamber 138 through recess 134 configured to receive a button 154 attached to the release member 142.

The handle 130 can accept insertion of the shaft 112 through hole 156 and into engagement with knob 150. Likewise, the spring 152 is biased so that depression of button 154 causes the rocker bar 148 to pivot and disengage knob 150 from notch 118 thereby allowing for removal of shaft 112. The instrument handle 130 can be formed from plastic or other suitable materials.

Figure 19:
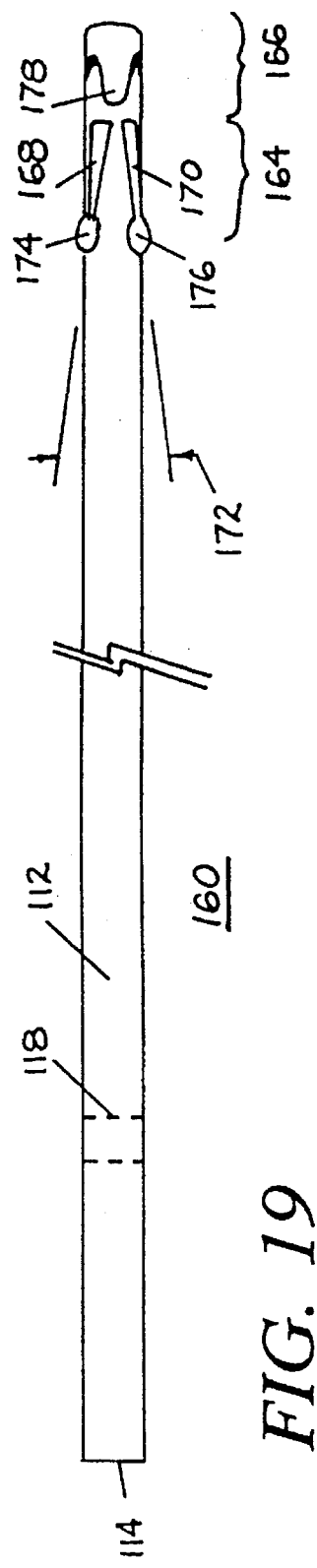
FIG. 19 is an end view illustrating the instrument of FIG. 18.

Referring now to FIGS. 18 and 19, an excision instrument 160 useful in performing a fasciectomy is now described. The excision instrument 160 includes an active or operative portion 162 located on the distal end 116 of shaft 112. The operative portion 162 has cutting section 164 and gathering section 166. The cutting section 164 has dual laterally spaced knife portions 168 and 170 extending transverse from the shaft 112. The knife portions 168 and 170 spread slightly at angle 172 for improving the cutting of tissue. The palpitation extensions 174 and 176 extend proximally beyond the knife portions 168 and 170 and are adapted to hook under and extravasate from the plantar fascia to palpitate the underlying fat pad during excision. The gathering section 166 has snagging member 178 that snags and removes cut tissue from the wake of cutting section 164. The excision instrument 160 can be used with sleeve member 22 or within the instrument portion 78 of member 54.

Figure 20:
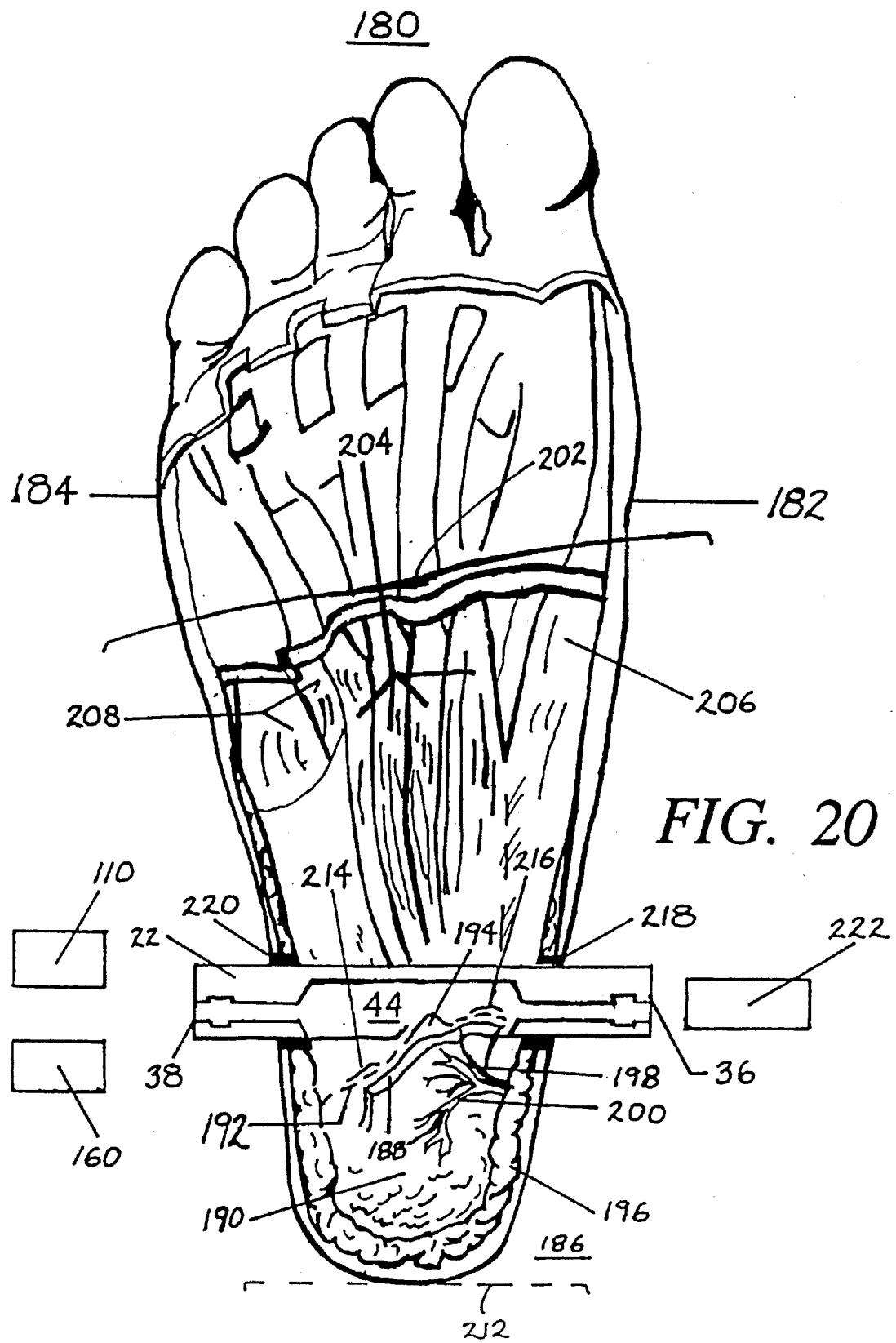
FIG. 20 is a plantar view of the foot illustrating the method for performing endoscopic heel surgery according to the present invention.
Figure 21B:
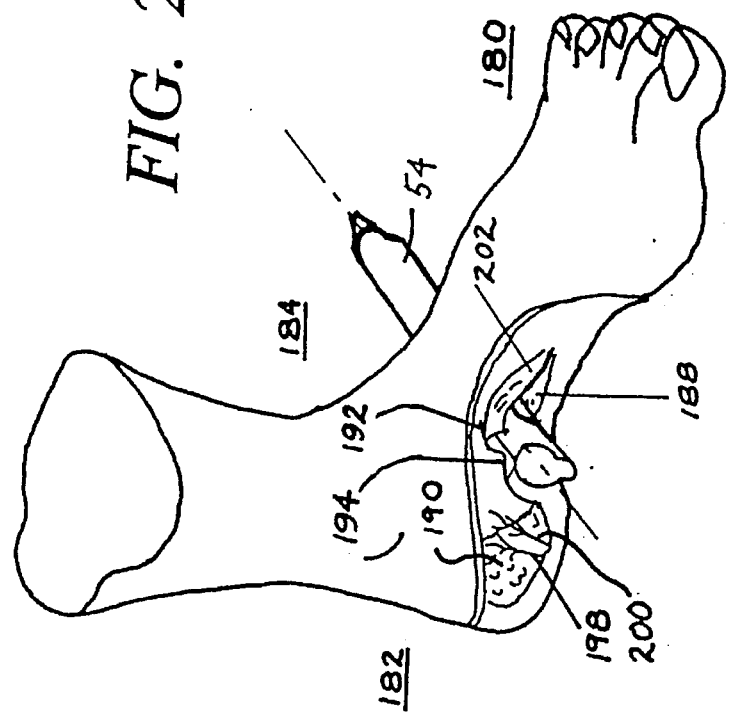
FIGS. 21a and 21b are perspective side views of the foot illustrating the placement of the system for endoscopic heel surgery according to the method of the present invention.
Figure 21A:
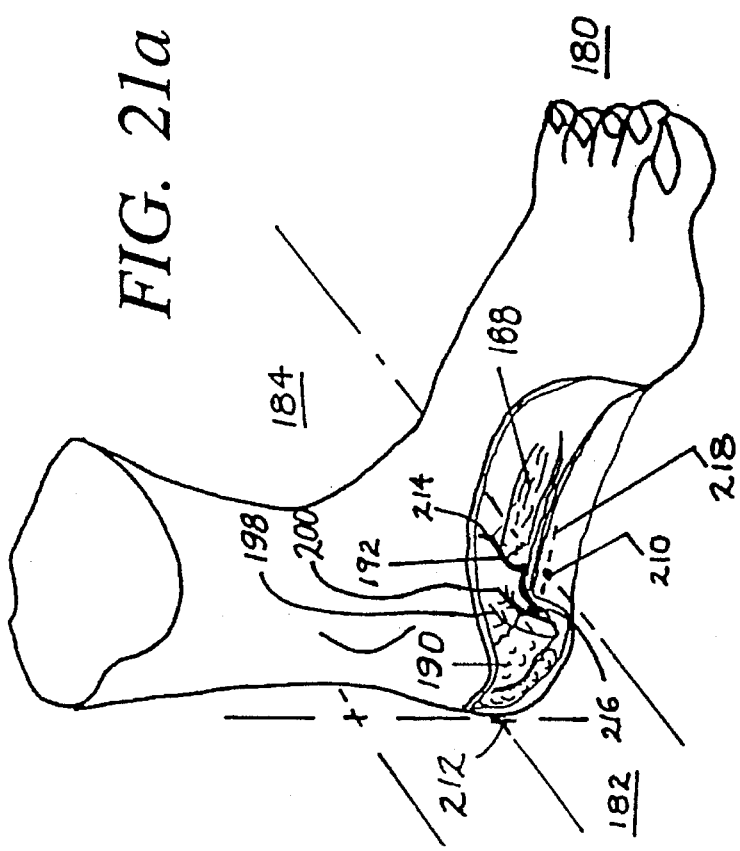

Referring now to FIGS. 20 and 21a and 21b, a procedure for performing endoscopic heel surgery according to the present invention is described. The patient is placed on the operating table in a prone position having the legs extending from the operating table with the feet dangling downwardly. The foot 180 is locally anesthetized and the skin cleaned for forming incisions. Alternatively, the knee can be flexed elevating the foot 180 with respect to the operating table to minimize impedance from the other leg and to manipulate the foot to substantiate the release of the plantar fascia.

The sleeve member 22 or 54 is driven into the foot 180 from a medial aspect 182 to a lateral aspect 184 of heel 186. The foot 180 is comprised of a web of compacted overlapping tissues such as, for example, plantar fascia 188 attached to the os calcis 190 at a line of insertion 192. At the line of insertion 192, a spur 194 can develop on the os calcis 190 from the pull and degeneration of plantar fascial tissue 188. A fat pad 196 overlies the os calcis 190 and has nerve branch 198 and vascular branch 200 interwoven therebetween. The plantar fascia 188 overlies muscles 202 including a flexor digitorum brevis group 204, abductus hallucis group 206 and abductus digiti minimi group 208.

The sleeve member 22 is positioned distal of the os calcis 190 and between the dorsal underlying plantar fascia 188 and superior muscles 202 avoiding the nerve and vascular branches 198 and 200, respectively. The portal 44 is positioned plantarly and superior to the plantar fascia 188 and distal of the os calcis 190 to provide access and visualization of the line of insertion 192. Visualization can be made with a standard 30 degree angulated 4.0 mm arthroscopic camera system 222. The portal 44 provides clear assessment of the plantar fascia 188, os calcis 190 at the line of insertion 192. Assessment of the belly and interface of the muscles 202 such as the abductus hallucis and digiti minimi muscles 206 and 208 and the nerve and vascular branches 198 and 200 also can be identified.

The camera system 222 is introduced through the open end 36 on the medial aspect 182 of the foot 180. The other open end 38 is used as a working portal for the introduction of various surgical instruments to operate caudally on the line of insertion 192 such as for the transection of the plantar fascia 188 and removal of spur 194 on the os calcis 190. Once the portal 44 is positioned adjacent the line of insertion 192 of the plantar fascia 188 into the os calcis 190, an endoscope can be inserted into open end 36 and an instrument into the other open end 38.

A first and second surgical operation is performed at the operative site. The obturator 24 is reinserted within the sleeve member 22 and this assembly is retracted while forcing plantarly the tip 94 or 96 of the obturator 24 again substantiating the complete division of the plantar fascia with the tip 94 or 96 coursing the fat pad 196 underneath the plantar fascia 188. The operative site is cleaned and lavaged with copious amounts of sterile saline. The entry and exit incisions 218 and 220 can be sutured closed with a solitary suture and dressed with a dry sterile compression dressing after successful performance of the desired surgical operations.

As illustrated in FIGS. 14 and 15, the fasciotomy instrument 110 can be used to divide caudally the plantar fascia 188 from the medial aspect 182 to lateral aspect 184 with visualization directed via the camera system 222. Direction of the medial to lateral division is made in the caudal approach to avoid damage to the nerve and vascular branches 198 and 200 located on the medial aspect 182 of the heel 186.

Alternatively, the fasciectomy instrument 160 can be used to excise caudally a section of plantar facial tissue 188 as illustrated in FIGS. 18 and 19. Extravasation of the palpitation extension 126 from the plantar fascia 188 and fat pad 196 can be felt through the shaft 112 and is an indication of the release of the plantar fascia 188. As is known in conventional surgical interventions, the release of the plantar fascia could be externally substantiated only by palpitation of the dorsal skin or flexure of the foot 180. Thus, the palpitation portion 126 has the advantage of providing an indication and feel of the release or total division of the plantar fascia 188 during transection. In addition, as the plantar fascia 188 is a thick tissue, the use of the expanded portal 44 has the advantages of enabling visualization of the deep cut apex of thick tissue.

In order to position sleeve member 22, a location 210 on the medial aspect 182 of the heel 186 is determined to avoid damage to the nerve branch 198 and vascular branch 200. The location 210 can be determined using a non-weight bearing lateral radiograph of the foot 180 and the marking system 230 described herein. The lateral radiograph can be used to measure and triangulate the distance between edge 212 and tuberoscopies 214 and 216 of the os calcis 190. An entry incision 218 is made on the medial aspect 182 of the heel 186 at the determined location 210, as shown in FIG. 21a. The size of the entry incision 218 can vary, for example, incisions ranging from 2 cm to 4 cm.

A channel between tissue and bone can be formed by driving the obturator 24 and the sleeve member 22 assembly through the entry incision 218 from medial to lateral until the surgeon can see tenting of the skin on the lateral aspect 184 of foot 180, as shown in FIG. 21b. The tip 94 or 96 forms the channel by bluntly separating the plantar fascia 188 from muscles 202 and other surrounding soft tissue both superiorly and inferiorly. An exit incision 220 is made at the location of the tented skin with the assembly passed through the foot. The portal 44 should be positioned superior to the plantar fascia 188 and adjacent the os calcis 190 before removing the obturator 24. Thus, an advantage is that the nerve and vascular branches 198 and 200 can be visualized and avoided.

As illustrated in FIGS. 22 and 23, the location 210 for insertion of the obturator 24 and the sleeve member 22 assembly can be determined before surgery by visualizing using a lateral radiograph or x-ray of the foot 180 to identify the location of tuberoscopies 214 and 216 or spur 194 such as the distal tubercle margin of the os calcis 190.

The marking and insertion system 230 of the present invention can be use in conjunction with the lateral radiograph for precise insertion of the assembly avoiding damage to neurovascular structures 198 and 200. The system 230 includes a heel holding member 232, location member 234 and insertion member 236. The heel holding member 232 can attach and use the location member 234 for no-sterile or non-surgical site use to determine location 210 prior to surgery. The heel holding member 232 can then attach and use the insertion member 236 in the surgical setting. The location member 234 is calibrated correspondingly with the insertion member 236 so that the location 210 determined by the location member 234 has a corresponding location on the insertion member 236.

The system 230 can be formed from suitable materials such as a radiograph opaque plastic or the like. The generally L-shaped heel holding member 232 has a base portion 238 releasably attached to an end portion 240 to keep the foot in a neutral position such as 90 degrees. The end portion 240 can be attached to either side of the base portion 238 using thumb screws 242 allowing adaptation of either a right or left foot. Likewise, location member 234 can be attached to the base portion 238 using thumb screws 242 and allows interchanging the location member 234 for either foot. the location member 234 includes a reference scale 244 laminated or otherwise disposed within the opaque plastic of the location member 234 to superimpose or capture the reference scale 244 on the lateral radiograph for use in marking the location 210 for making the entry incision 218.

As shown in FIGS. 24a and 24b, 25 and 26, the insertion member 236 includes a grid portion 246 corresponding to the reference scale 244 for use in inserting a guide wire or pin 248. It is important to measure the distance between the edge of the skin on the heel 186 such as the skin abutting the end portion 240 the distal edge of the os calois 190. Thus, the coordinates of the determined location 210 on the lateral radiograph can be transferred to the grid portion 246 to insert guide wire 248. In order to prepare the foot 180 for the lateral radiograph, the foot is positioned in the heel holding member 232 with the medial aspect abutting the location member 234.

As shown in FIGS. 24a and 24b through 26, the location member 234 is interchanged with the insertion member 236 at the time of surgery. The insertion member 236 includes elongated guide tubes 250 arranged and calibrated to correspond to the grid portion 246. The guide wire 248 is inserted into the guide tube 250 corresponding to location 210. The elongated guide tubes 250 provide for insertion of the pin 248 from the medial 182 to lateral 184. Once through the foot, the system 230 using the insertion member 236 can be removed from the medial extension of guide wire 248 thereby leaving the guide wire in the foot. The obturator 24 and sleeve member 24 can use the guide wire 248 as to guide the medial to lateral separation of tissue. Likewise, the bore 86 can be configured to receive the guide wire 248 and follow the predefined path of guide wire 248. Once the sleeve member 24 or 54 is properly positioned, the guide wire 248 can be removed from the lateral side 184 of the foot 180. Thus, the marking and insertion system 230 of the present invention can be used advantageously to locate more precisely the entry incision 218 and avoid damage to neurovascular structures 198 and 200, and likewise be used adaptively to insert guide pin 248 through the foot 180.

Referring to FIGS. 27-29, an alternate embodiment of a surgical instrument generally indicated at 250, particularly configured to divide the plantar fascia, in accordance with the method of the present invention is illustrated. The instrument 250 is particularly suited for insertion into the sleeve member 22 and dividing the plantar fascia. The instrument includes a forward elongated handle portion 252 and an elongated shaft 254 which is aligned with the handle 252 to define a longitudinal axis 256. The handle forms a notch 260 which extends along a portion of the length of the handle.

A knife blade generally indicated at 262, is attached at a distal end 254a of the shaft 254 opposite the handle 252. The knife blade 262 is particularly suited for dividing the plantar fascia without snagging, and during the dividing process, palpitating the underlying tissue to prevent damage thereto. The knife blade includes a knife edge 264 at a forward end 262a of the blade 262. The knife edge 264 is sharpened and extends for at least a portion of the forward edge 262a of the blade. Handle 252 desirably may include a relief portion in the area from which shaft 254 protrudes to permit the shaft and knife blade 262 to extend into sleeve member 22 without handle 252 abutting the end of the sleeve member.

To prevent snagging of the plantar fascia, the knife edge 264 is preferably configured to extend outward and rearward from an upper surface 270 of the shaft 254. The edge 264 forms an angle "A" with an longitudinal axis 256 with "A" being preferably an obtuse angle relative to the axis 256. It is contemplated that the angle "A" may vary with a preferred angle being approximately 120 degrees.

The blade 262 includes lateral side faces 268 which are preferably planar and angled laterally outward from the edge 264 to a rear end 262b of the blade 262. Referring in particular to FIG. 29, the angle side faces 268 gives the blade 262 an appearance of a triangle in top plan view with the apex being the front edge 264 and the base of the triangle being the rear 262b.

The blade 262 also includes a top or end surface 270 which is preferably a polished smooth planar or generally rounded surface. The surface 270 ends rearward generally parallel to the longitudinal axis 256 and has a planar configuration formed in the shape of a triangle. The smooth upper surface 270 palpitates tissue underlying the plantar fascia to prevent dividing of that tissue. The blade 262 extends upward from a landing 274 which is angled relative to the longitudinal axis 256. The angle of the landing 274 facilitates the dividing of the tissue without snagging of the blade 262 on the tissues.

Referring to FIG. 30, an alternate embodiment of a knife blade, generally indicated at 290 for the surgical instrument 250 is illustrated. In this embodiment, knife blade 290 is also particularly suited for dividing the plantar fascia without snagging and for palpitating the underlying tissue so as to prevent damage to that tissue. Blade 290 includes a knife edge 292 at a forward end 290a of blade 290, and as in the embodiment of the surgical instrument 250 with knife blade 262, in this embodiment knife edge 292 similarly forms an angle "A" with the longitudinal axis 256, with "A" preferably being an obtuse angle relative to the axis 256, and is contemplated to vary with a preferred angle being approximately 120 degrees.

Also as in the previous embodiment, knife blade 290 includes lateral side faces 294 (only one is shown, the other being a mirror image of the face shown and positioned on the opposite side of blade 290). However, faces 294 do not extend to the junction with shaft 254 or to the upper surface 296 of blade 290. Faces 294 are preferably planar and form a shallower and shorter knife edge 292 than edge 264 of blade 262, as shown in FIG. 30. With this configuration, upper surface 296 of shaft 254, and hence of blade 290, is wider and more blunt than upper surface 270 of blade 262, and more readily palpitates without dividing the underlying tissue while dividing the plantar fascia. The lower edges 298 of the lateral side faces 294 further facilitates the dividing of the tissue without snagging of the tissues.

Figure 31:
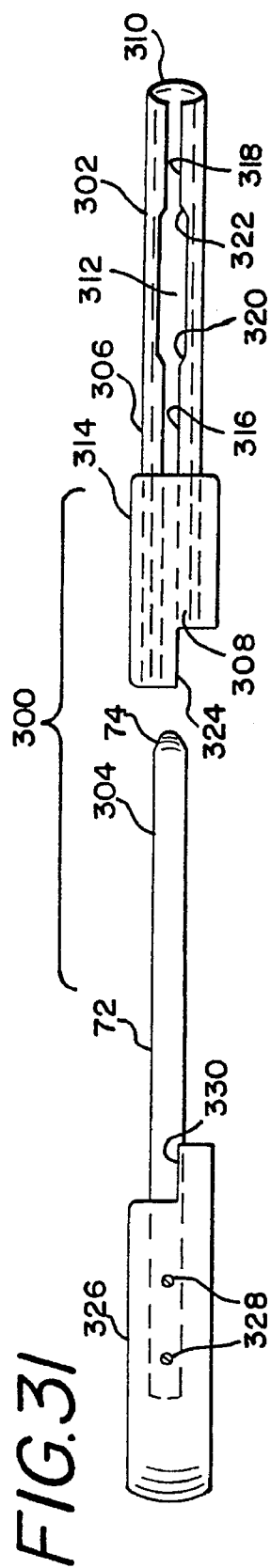
FIG. 31 is an elevational view illustrating an alternate embodiment of a sleeve member and obturator of the present invention featuring a locking system therebetween.

Referring to FIG. 31, an alternate embodiment of a preferred method and system of the present invention for the performance of endoscopic procedures on the body is illustrated, with particular application to relieve heel pain in a foot. As heretofore described with respect to the embodiment of FIGS. 1-26, the embodiment can by used in the environment for treatment of the painful heel syndrome which can include neuritis, myositis, fascitis and adventitial bursiris with or without a calcaneal spur. The endoscopic system 300 of this embodiment of the present invention includes a cannula or sleeve member 302 and a trocar or obturator 304. As shown, sleeve member 302 includes an elongated tube 306 with open ends 308 and 310, an opening or window 312 in the side of tube 306, and a hub or collar 314 which acts as a stop member as will be hereinafter described. Sleeve member 302 may optionally include slot segments 316 and 318, which, if present, may be connected to window 312 by tapered portions 320 and 322. As shown, slot segments 316 and 318 may extend to the open ends 308 and 310 of tube 306. As in the case of sleeve member 22 heretofore described, window 312 provides access to view heel structures, such as the os calcis, neurovascular structures and plantar fascia, as well as spurs on the os calcis, upon sleeve member 302 being placed in the patient's foot.

Further as in the case of sleeve member 22, sleeve member 302 allows an endoscope to be placed in either open end or portal 308 or 310 to form an image of the interior heel structures. These open ends or portals also allow instruments to be placed therethrough in order to perform surgical procedures on the heel structures. Also as in the case of sleeve member 22, sleeve member 302 is desirably made to extend from either side of the foot to the other, and can be made of the same materials as sleeve member 22.

The hub or collar 314 is secured to end 308 of tube 306 and provides both a stop member to prevent end 308 from entering the entry incision in the foot, and a grip when manipulating sleeve member 302 or an instrument placed therein. Collar 314 is formed with an outwardly facing, generally flat centered surface 324 which extends axially from the open end 308 of tube 306. Surface 324 is axially relieved for the purpose of receiving obturator 304 and instruments as will be hereinafter described.

Obturator 304 is generally similar to obturator 24 previously described, and reference numerals of elements common to both are used in FIG. 31 without further description. Sleeve member 302 slidably receives the shaft 72 of obturator 304 along the length of tube 306 with the blunt distal end 74 protruding from end 310. Obturator 304 includes a handle 326 which may be affixed to shaft 72 by means of fasteners, such as rivets 328, or by other fastening means, including adhesives, known generally to the medical instrument art. Handle 326 further includes a flat surface 330 which is configured to engage surface 324 of collar 314 upon shaft 72 being inserted into and through open end 308 of tube 306 and being engaged against relative rotation between obturator 304 and sleeve member 302 when shaft 72 is fully inserted into sleeve member 302. In this manner sleeve member 302 can be rotated within a channel formed in the foot by rotating handle 326 to position window 312 in a desired position.

Figure 32:
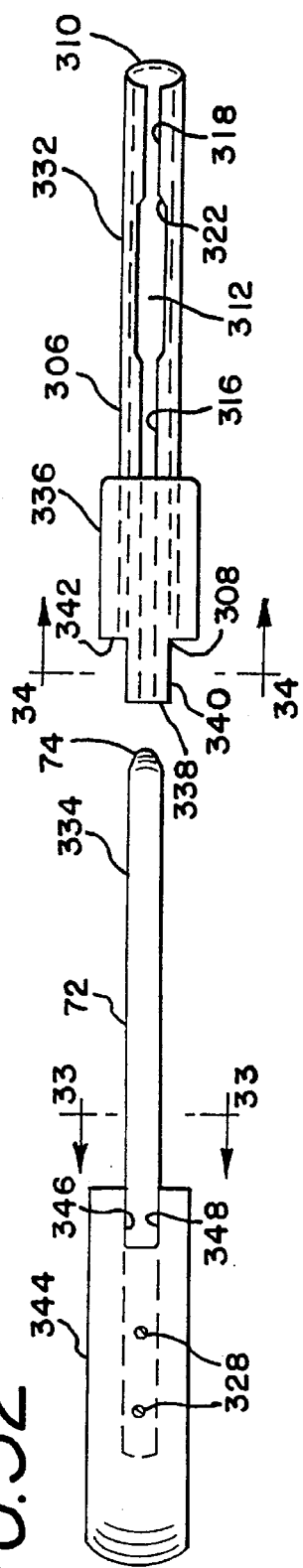
FIG. 32 is a view similar to FIG. 31, illustrating another alternate embodiment of a sleeve member and obturator of the present invention with an alternate locking system therebetween.
Figure 33:
FIG. 33 is a cross-sectional view taken along lines 33—33 of FIG. 32 showing the alternate locking system.
Figure 34:
FIG. 34 is a cross-sectional view taken along lines 34—34 of FIG. 32 showing another view of the alternate locking system.

Referring to FIG. 32–34, another alternate embodiment of a preferred method and system of the present invention for the performance of endoscopic procedures on the body is illustrated, which is similar in may respects to the embodiment shown in FIG. 31, and the same reference numerals have been utilized for common elements without further description. The purpose and objects of this embodiment is the same as those described in connection with the embodiment illustrated in FIG. 31. In this embodiment, sleeve member 332 is adapted to engage obturator 334 in a manner similar to that shown for sleeve member 302 and obturator 304 in the previous embodiment.

A collar 336 is provided secured to sleeve member 332 which has a narrowed portion 338 extending axially from tube 306, and may include opening 308, and includes a flat surface 340 at least on one side, as shown, or on both sides, not shown. Narrowed portion 338 may also be square in cross-section, with all sides flat, also not shown. Collar 336 includes abutment surfaces 342 from which narrowed portion 338 extends. Obturator 334 has a handle 344 which is similar to handle 326, but has a recess 346 surrounding shaft 72 configured to receive narrowed portion 338 of collar 336 when shaft 72 is received in tube 306 of sleeve member 332. Recess 346 of handle 344 includes at least one flat surface 348 adapted to engage flat surface 340 of collar 336 and prevent relative rotation between sleeve member 332 and obturator 334 when so engaged with shaft 72 received in tube 306. Recess 346 may have more than one flat side, and may be square with all flat sides to conform to the configuration of narrowed portion 338 of collar 336.

Using the system illustrated in FIGS. 31 or 32–34 described herein, the procedure for performing endoscopic surgery in a patient to relieve heel pain heretofore described can be advantageously performed. The procedure can be performed by forming an entry incision on one side of the foot and forming a channel in the foot extending interiorly of the entry incision between the os fascia, plantar fascia and the aponeurotic fibers of the muscles by bluntly separating the muscle belly or plantar fascia from surrounding soft tissue, while avoiding injury to the vascular and neural structures in the heel, by inserting and advancing through the entry incision obturator 304 or 334 engaged in sleeve member 302 or 332, respectively, as heretofore described. An exit incision is made, preferably where the blunt end 74 of the obturator has caused the skin to tent at a point opposite the entry incision when the obturator and sleeve member assembly is driven through the foot. The channel is extended through the exit excision by passing blunt distal end 74 of the obturator 304 or 334 and the end 310 of sleeve member 302 or 332 through the exit incision. Sleeve member 302 or 334 is positioned in the channel with the window 312 facing the interior surface of the foot in a selected direction, preferably by rotating the sleeve member in the channel by rotating obturator 304 or 334 while positioned in the sleeve member. In such preferred use, obturator 304 or 334 is next withdrawn from the sleeve member, and an instrument, used for excising a portion of the foot structure is passed through either one of the portals 308 or 310. A suitable instrument for this purpose can be the instrument shown in U.S. Pat. No. 5,029,573, issued to James C. Chow on Jul. 9, 1991, or, if desired, the instrument illustrated in FIGS. 27–29 or 30, and described herein. The instrument is positioned the excising portion thereof adjacent the portion of the foot structure to be excised through window 312 and manipulated to extend the excising portion thereof through window 312 and to excise the portion of the foot structure as desired.

In a particular procedure to relieve heel pain in a foot by decompression of the first branch of the lateral plantar nerve, an entry incision is made between the os calceus, plantar fascia and the aponeurotic fibers of the muscles by separating the muscle belly or plantar fascia from surrounding soft tissue and forming a channel therethrough, while avoiding injury to the vascular and neural structures in the heel, using the procedure described above. Sleeve member 302 or 332 is positioned, also as described above, with the window of the sleeve facing the inferior surface of the calcaneus. Obturator 304 or 334 is withdrawn from the sleeve member, and an instrument used for cutting tissue, also described above, is passed through one of the portals of the sleeve member, and is positioned with the cutting portion thereof adjacent an inferior surface of the calcaneus through window 312 of the sleeve member. The handle of the instrument is manipulated to extend the cutting portion thereof through window 312 and to excise the inferior and lateral wall of the abductor hallucis fascia. Other procedures described herein can also be preformed using sleeve member and obturator assembly 300 with desirable results.

Many modifications and variations of the present invention are possible in light of the above teachings. Thus, it is to be understood that, within the scope of the appended claims, the invention may be practiced otherwise than as specifically described above.

What is claimed is:

1. An instrument for use in cutting tissue, comprising:
   a. an elongated shaft having proximal and distal ends;
   b. a handle secured to said proximal end;
   c. said distal end having a forward portion having generally rounded corners and extending generally transversely from said shaft, a cutting portion, and means at a lower end of said cutting portion for guiding said forward portion without exposing said cutting portion to the tissue while guiding the instrument.

2. The instrument of claim 1, wherein said means for guiding forming with said shaft and forward portion a hook portion extending generally transversely from said shaft and enclosing said cutting portion within the interior of said hook portion.

3. The instrument of claim 2, wherein said hook portion has a distal end portion as said means for guiding and said distal end portion extends substantially parallel to said shaft.

4. The instrument of claim 3, wherein said distal end portion of said hook portion extends proximally beyond said cutting portion.

5. The instrument of claim 4, wherein said cutting portion includes a knife portion having a concave shape.

6. The instrument of claim 4, wherein said cutting portion includes a knife portion having a straight shape and said knife portion and said forward end are angled relative to the elongated shaft.

7. An instrument for use in cutting tissue, said instrument comprising:
   a. an elongated shaft having proximal and distal ends;
   b. a handle attachable to said proximal end;
   c. locking means at said proximal end for releasably attaching a handle to said shaft, and
   d. said distal end having a forward portion having generally rounded corners and extending generally transversely from said shaft, a cutting portion, and means at a lower end of said cutting portion for guiding said forward portion without exposing said cutting portion to the tissue while guiding the instrument.

8. The instrument of claim 7, wherein said knife blade includes an end surface which is generally parallel to said elongated shaft and said knife edge extends along the forward edge of the knife blade less than the entire distance between the elongated shaft and said end surface.

9. The instrument of claim 8, wherein said knife edge is spaced from said elongated shaft.

10. The instrument of claim 8, wherein said knife edge is spaced from said end surface.

11. An instrument for use in cutting tissue, comprising:
    a. an elongated shaft having proximal and distal ends;
    b. a handle secured to said proximal end;
    c. said distal end having a forward portion including a knife blade extending at an angle from said elongated shaft, and
    d. said knife blade including a proximally facing knife edge extending for at least a portion of and along the forward edge of the knife blade.

12. The instrument of claim 11, wherein said knife edge forms an obtuse angle relative to said elongates shaft.

13. The instrument of claim 12, wherein said knife edge extends from said elongated shaft at an angle of approximately 120 degrees.

14. The instrument of claim 11, wherein said knife blade includes at least one substantially planar lateral side face angled laterally outwardly from said knife edge.

15. The instrument of claim 14, wherein said knife blade includes a pair of substantially planar lateral side faces, angled laterally outwardly from said knife edge.

16. The instrument of claim 11, wherein said knife blade includes an end surface which is generally parallel to said elongated shaft.

17. The instrument of claim 16, wherein said end surface is substantially planar.

18. The instrument of claim 16, wherein said end surface is generally rounded.

19. The instrument of claim 11, wherein said knife blade includes an end surface which is generally parallel to said elongated shaft, and a pair of substantially planar lateral side surfaces angled laterally outwardly from said knife edge, and said knife edge forms an obtuse angle relative to said elongated shaft and is spaced from both said elongated shaft and said end surface.

20. A procedure for performing endoscopic surgery in a patient to relieve heel pain in a foot, the foot having a heel with skin, fat pad, plantar fascia, os calcis bone, vascular and neural structures, including the first branch of the lateral plantar nerve, and muscles including flexor digitorum brevis, abductus hallucis, and abductus digiti minimi, the procedure comprising the steps of:
    a. forming an entry incision on one side of the foot;
    b. forming a channel in the foot extending interiorly of said entry incision between the os fascia, plantar fascia and the aponeurotic fibers of the muscles, said channel avoiding the vascular and neural structures in the heel, said channel being formed by inserting and advancing through said entry incision a detachable obturator and sleeve member assembly, the obturator having a blunt distal end and the sleeve member having portals at either end portion thereof through which portions of the obturator and at least one instrument may pass and at least one window area through which a portion of the at least one instrument may be exposed to the interior structure of the heel;
    c. forming an exit incision for a portion of the obturator and sleeve member assembly at the side of the foot opposite the entry incision, and extending the channel through the exit excision by passing the blunt distal end of the obturator and the end portion of the sleeve member adjacent thereto through the exit incision;
    d. positioning the obturator and sleeve member assembly in the channel with the window of the sleeve facing the surgical site;
    e. withdrawing the obturator from the sleeve member;
    f. inserting an instrument for performing a surgical procedure on the foot through one of the portals of the sleeve member;
    g. positioning the instrument for performing a surgical procedure on the foot adjacent the surgical site for performing the surgical procedure through the window of the sleeve member, and manipulating the instrument to perform the surgical procedure.

21. The procedure of claim 20 further including:
    a. determining the location of a spur to be reduced which is accessible through the window of the sleeve member;

b. wherein the instrument for performing a surgical procedure on the foot is an instrument used for reducing a spur and is inserted into the sleeve member and is positioned with the reducing portion thereof adjacent the spur to be reduced through the window of the sleeve member; and c. manipulating the instrument by extending the reducing portion thereof through the window and using the instrument to reduce the spur.

22. The procedure of claim 21 wherein the location of the spur is determined by at least one radiograph.

23. The procedure of claim 21 wherein the location of the spur is determined by inserting an endoscope through one of the portals of the sleeve member and locating the spur.

24. The procedure of claim 21 wherein the instrument used for reducing a spur is a bone resector, and the spur is reduced by resection.

25. The procedure of claim 21 wherein a tissue resector instrument is inserted into the sleeve member and is positioned with the resecting portion thereof adjacent excessive soft tissue associated with the spur to be reduced through the window of the sleeve member, and the tissue resector instrument is extended and manipulated through the window and using the instrument to remove the excessive soft tissue associated with the spur.

26. The procedure of claim 20 wherein:

a. the positioning the sleeve member in the channel comprises positioning the sleeve member with the window of the sleeve member facing the inferior surface of the calcaneus;

b. wherein the instrument for performing a surgical procedure on the foot is an instrument used for excising and is inserted into the sleeve member and is positioned with the excising portion thereof adjacent an inferior surface of the calcaneus through the window of the sleeve member; and c. manipulating the instrument by extending the excising portion thereof through the window and excising the inferior and lateral wall of the abductor hallucis fascia.

27. The procedure of claim 20 wherein the instrument for performing a surgical procedure on the foot has a blunt portion and the blunt portion is positioned and extended through the window of the sleeve member to simultaneously divide caudally the plantar fascia and palpitate a fat pad underneath the plantar fascia.

28. The procedure of claim 20 wherein prior to performing a surgical procedure on the foot, an instrument having a blunt portion is positioned and extended through the window of the sleeve member to simultaneously divide caudally the plantar fascia and palpitate a fat pad underneath the plantar fascia.

29. The procedure of claim 20 wherein:

a. the positioning the sleeve member in the channel comprises positioning the sleeve member with the window of the sleeve member facing the inferior surface of the calcaneus;

b. wherein the instrument for performing a surgical procedure on the foot is an instrument used for dividing and is inserted into the sleeve member and is positioned with the dividing portion thereof adjacent an inferior surface of the calcaneus through the window of the sleeve member; and c. manipulating the instrument by extending the dividing portion thereof through the window and dividing the inferior and lateral wall of the abductor hallucis fascia.

30. The procedure of claim 20 wherein following withdrawal of the obturator, an endoscope is inserted through one of the end openings of the sleeve member and positioned at the window of the sleeve member for visual observation of the surgical site during the performance of subsequent surgical procedures.

31. The procedure of claim 20 wherein irrigation means are provided through one of the end openings of the sleeve member and directed at a surgical site through the window of the sleeve member during the performance of a surgical procedure.

32. The procedure of claim 20 wherein means for removing excised material from a surgical site is provided through one of the end openings of the sleeve member and at a surgical site through the window of the sleeve member during the performance of a surgical procedure.

33. The procedure of claim 32 wherein the means for removing excised material is a suction device.

34. The procedure of claim 32 wherein the means for removing excised material is a forceps device.

35. The procedure of claim 20 wherein:

a. the positioning the sleeve member in the channel comprises positioning the sleeve member with the window of the sleeve member facing tissue to be biopsied;

b. wherein the instrument for performing a surgical procedure on the foot is biopsy instrument used for excising a portion of tissue to be biopsied and is inserted into the sleeve member and is positioned with the excising portion thereof adjacent the tissue to be biopsied through the window of the sleeve member; and c. manipulating the instrument by extending the excising portion thereof through the window and excising the tissue.

36. The procedure of claim 35 wherein the biopsy instrument is a basket forceps.

* * * * *